United States Patent
Bormann et al.

(10) Patent No.: US 8,440,085 B2
(45) Date of Patent: May 14, 2013

(54) PLASMA SEPARATION

(75) Inventors: Thomas J. Bormann, Huntington, NY (US); Mikhail Fomovsky, Port Washington, NY (US); Galina Fomovska, Port Washington, NY (US)

(73) Assignee: Pall Corporation, Port Washington, NY (US)

( * ) Notice: Subject to any disclaimer, the term of this patent is extended or adjusted under 35 U.S.C. 154(b) by 32 days.

(21) Appl. No.: 13/153,586

(22) Filed: Jun. 6, 2011

(65) Prior Publication Data

US 2012/0305500 A1 Dec. 6, 2012

(51) Int. Cl.
*B01D 61/14* (2006.01)
*B01D 61/18* (2006.01)
*B01D 69/06* (2006.01)
*B01D 63/08* (2006.01)

(52) U.S. Cl.
USPC ............... 210/651; 210/321.6; 210/321.75; 210/321.84; 210/433.1; 210/436; 210/472; 210/483; 210/488; 210/489; 210/503; 210/505

(58) Field of Classification Search ............... 210/645, 210/650, 651, 652, 653, 767.1, 120, 180, 210/188, 203, 252, 258, 307, 321.6, 321.75, 210/321.84, 433.1, 436, 472, 483, 488, 489, 210/490, 491, 503, 504, 505, 506, 507, 508, 210/808
See application file for complete search history.

(56) References Cited

U.S. PATENT DOCUMENTS

| | | | | |
|---|---|---|---|---|
| 4,343,705 A * | 8/1982 | Legg | | 210/637 |
| 5,183,569 A * | 2/1993 | Kyriacou | | 210/636 |
| 5,242,384 A | 9/1993 | Robinson et al. | | |
| 5,472,605 A * | 12/1995 | Zuk, Jr. | | 210/436 |
| 5,707,520 A * | 1/1998 | Kuroki et al. | | 210/436 |
| 5,776,338 A * | 7/1998 | Mari | | 210/252 |
| 5,798,041 A * | 8/1998 | Zuk, Jr. | | 210/456 |
| 5,996,811 A | 12/1999 | Kitajima et al. | | |
| 6,170,671 B1 | 1/2001 | Kitajima et al. | | |
| 6,612,447 B1 * | 9/2003 | Breillatt et al. | | 210/489 |
| 6,659,288 B2 * | 12/2003 | Amano et al. | | 210/406 |
| 6,849,185 B1 | 2/2005 | Wu et al. | | |
| 7,048,855 B2 * | 5/2006 | de la Cruz | | 210/321.74 |
| 7,407,742 B2 | 8/2008 | Ikeda | | |
| 2008/0128341 A1 | 6/2008 | Jang et al. | | |
| 2009/0120865 A1 | 5/2009 | Chung et al. | | |
| 2010/0012577 A1 * | 1/2010 | Krause et al. | | 210/500.23 |

FOREIGN PATENT DOCUMENTS

DE 10157569 A1 6/2003
EP 1 580 551 A1 9/2005
WO WO 01/12325 A1 2/2001

OTHER PUBLICATIONS

Shim et al., "An on-chip whole blood/plasma separator with bead-packed microchannel on COC polymer," *Biomed Microdevices*, (12), pp. 949-957 (2010).
Extended European Search Report, Application No. 12169242.0, dated Sep. 17, 2012.
Singapore Search Report, Application No. 201203930-1, dated Dec. 26, 2012.

* cited by examiner

*Primary Examiner* — John Kim
(74) *Attorney, Agent, or Firm* — Leydig, Voit & Mayer, Ltd.

(57) ABSTRACT

Devices and methods for separating plasma from biological fluids such as blood and blood products are disclosed.

9 Claims, 7 Drawing Sheets

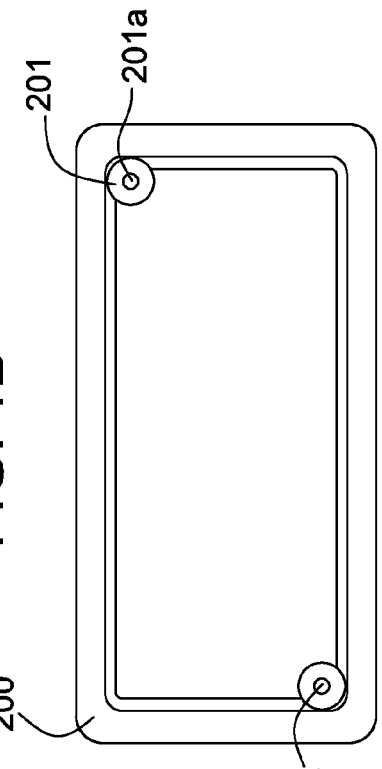
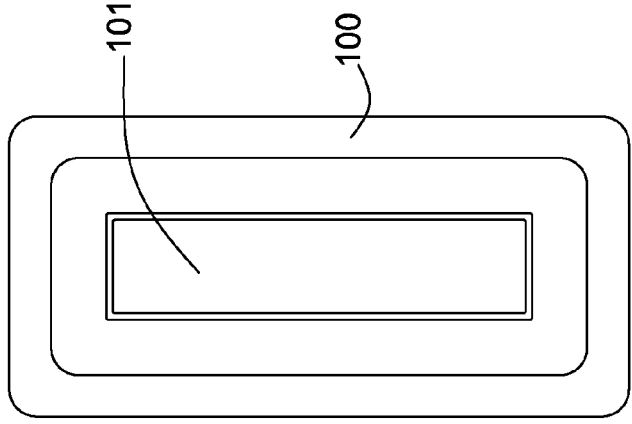
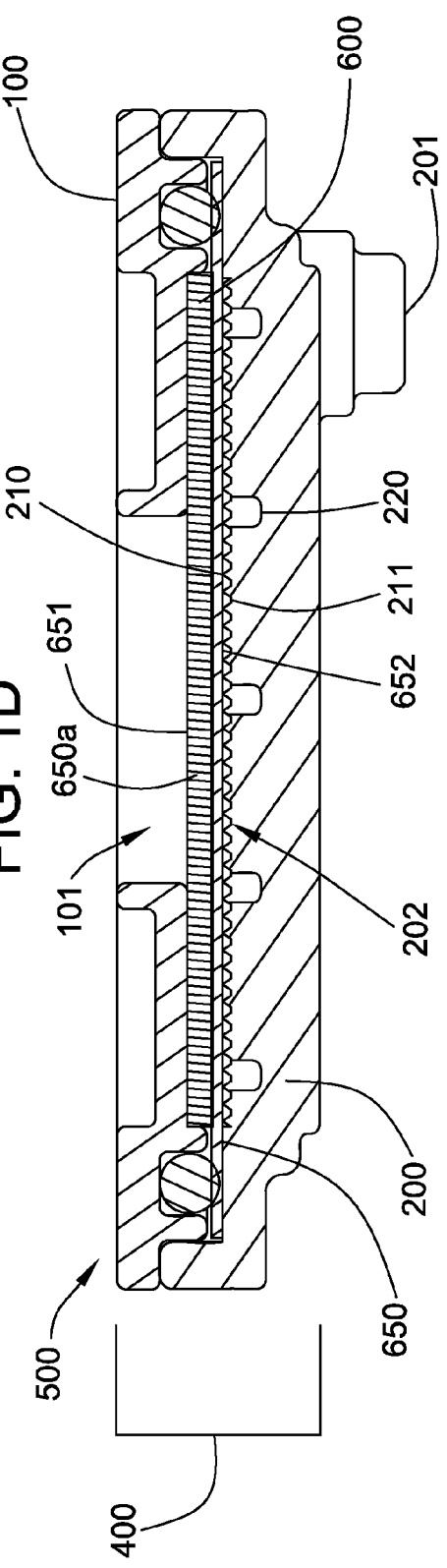

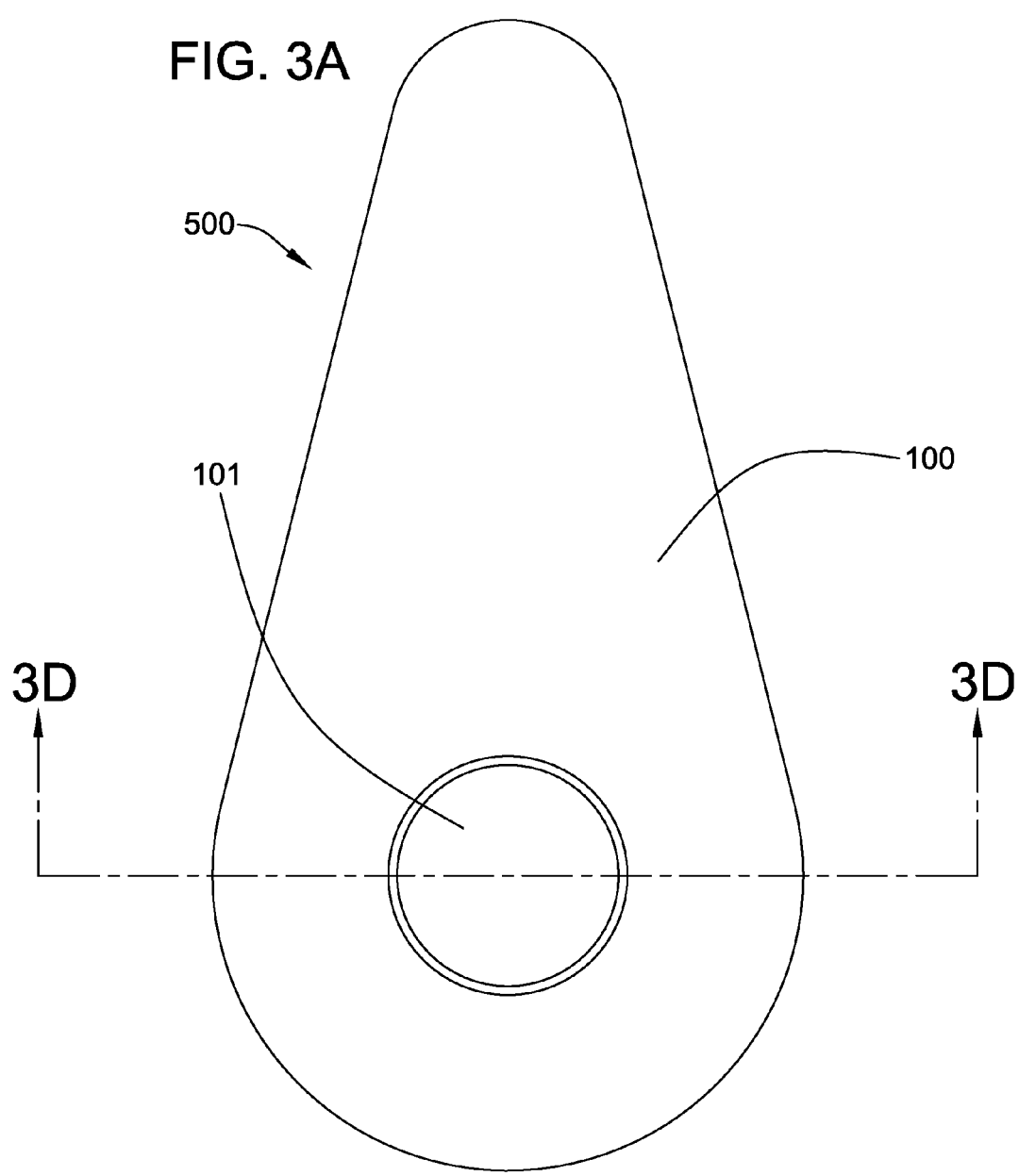
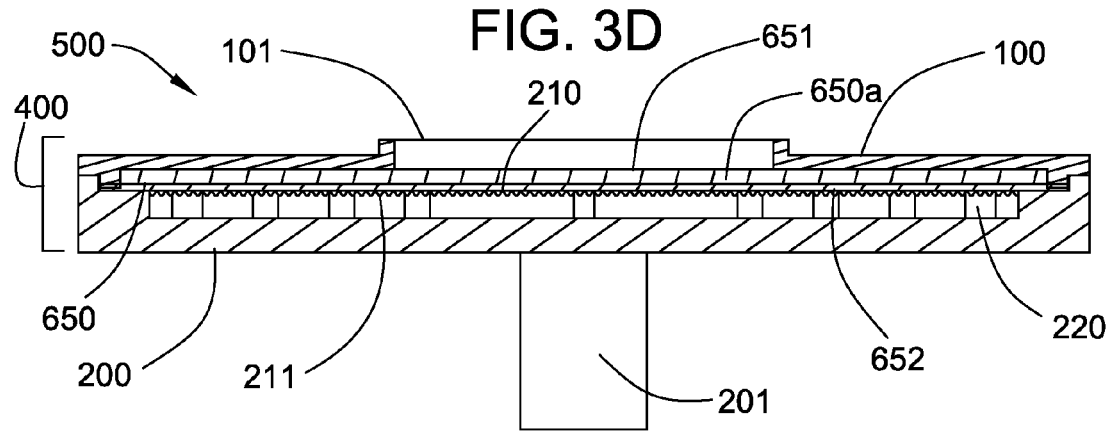

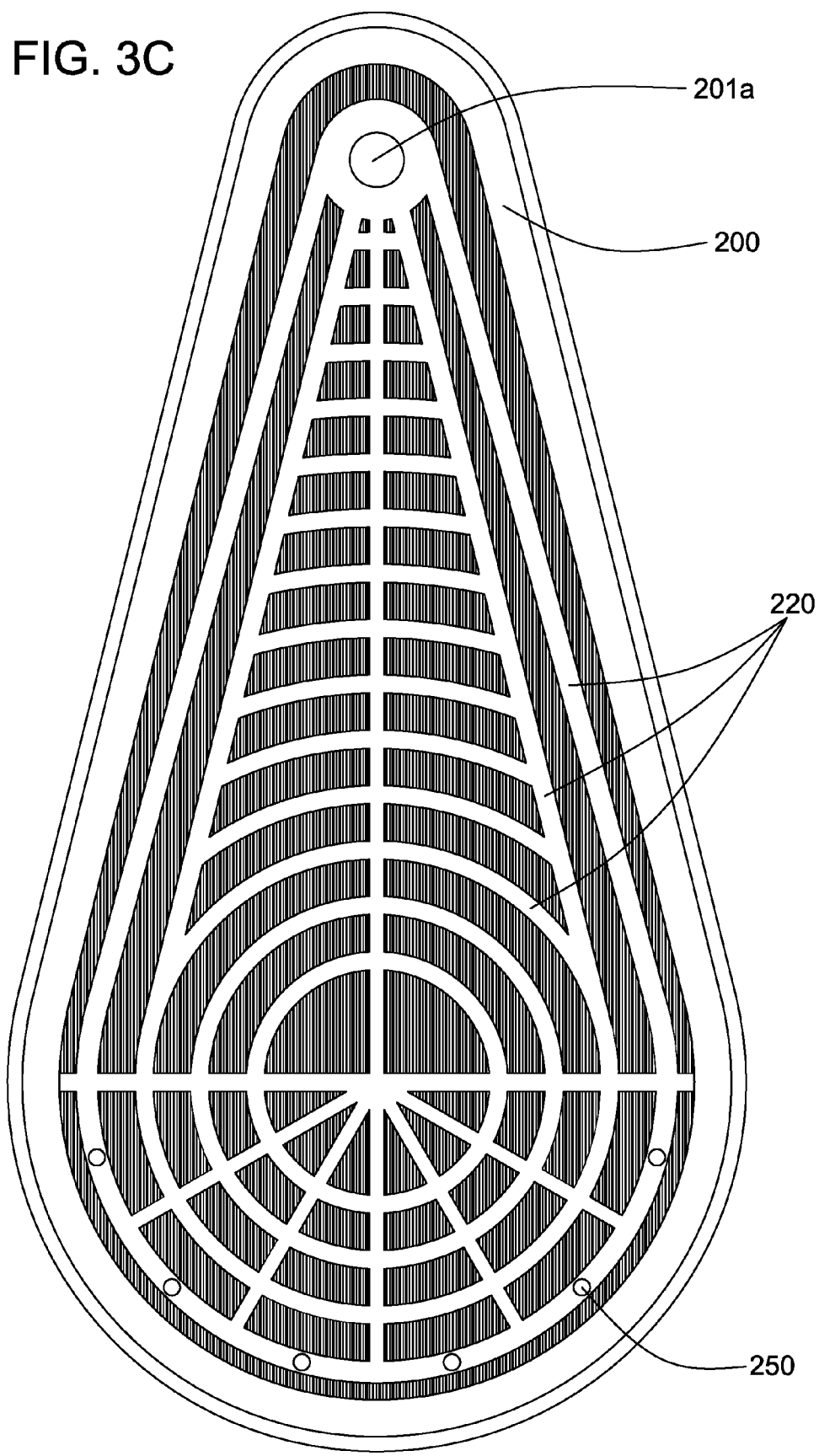

PLASMA SEPARATION

BACKGROUND OF THE INVENTION

A variety of tests for diagnosing disease, monitoring the course of disease and/or determining the effectiveness of treatment of a disease, involve obtaining plasma from a patient and performing tests on the plasma. Typically, blood is obtained from patient and processed to remove the cellular components to provide the plasma, wherein the processing includes (a) centrifuging the blood at high G forces for about 5-15 minutes so that the more dense cellular components can be concentrated at the bottom of the centrifuge tube, and the supernatant plasma can be removed, or (b) applying a few drops of blood to a lateral flow device wherein gravity and capillary forces provide for separating the plasma from the other components, and the separated plasma is wicked into an absorbent pad wherein test reagents react with the plasma.

However, processing blood by centrifugation generally involves transporting the blood sample to centralized laboratories containing centrifuges, which are operated by skilled laboratory personnel. This is costly, as it is time and labor intensive. Alternatively, lateral flow devices, which can be utilized outside of the laboratory, and without requiring skilled personnel, cannot easily produce the liquid plasma sample that is desired by most state of the art and accurate diagnostic tests.

The present invention provides for ameliorating at least some of the disadvantages of the prior art. These and other advantages of the present invention will be apparent from the description as set forth below.

BRIEF SUMMARY OF THE INVENTION

The present invention provides for the isolation of a suitable volume of substantially cell-free liquid from a biological fluid without using a centrifuge.

An embodiment of the invention provides a plasma separation device comprising: (a) a filter having an upstream surface and a downstream surface, the filter comprising a microporous membrane; and, (b) a housing, having an inlet, a downstream chamber, and an outlet, and at least one air channel; defining a fluid flow path between the inlet, the downstream chamber, and the outlet, with the filter disposed in the housing across the fluid flow path, wherein the outlet and the air channel are spaced apart and are arranged such that, when a negative pressure is created in the downstream chamber through the outlet, air passes into the downstream chamber via the air channel and sweeps plasma from the downstream surface of the filter and through the outlet. In some embodiments, the device includes two or more air channels and/or two or more plasma collection channels.

In another embodiment, a method for processing biological fluid is provided, comprising applying biological fluid to the upstream surface of the filter of an embodiment of the plasma separation device; passing plasma from the upstream surface of the filter to the downstream surface of the filter; creating a negative pressure in the downstream chamber through the outlet; passing air through the air channel into the downstream chamber and sweeping plasma from the downstream surface of the filter; and, passing swept plasma through the outlet.

BRIEF DESCRIPTION OF THE SEVERAL VIEWS OF THE DRAWING(S)

FIG. 1 is a view of an embodiment of a plasma separation device according to the present invention, where FIGS. 1A and 1B show top and bottom views, respectively, FIG. 1D shows a cross-sectional view, wherein the illustrated device has a single air channel, and the filter includes a membrane and an optional upstream fibrous medium.

FIG. 2 is a view of another embodiment of a plasma separation device according to the present invention, where

FIG. 3 is a view of another embodiment of a plasma separation device according to the present invention, where FIGS. 3A and 3B show top and bottom views, respectively, FIG. 3C shows a top view of the base, and FIGS. 3D and 3E shows cross-sectional views, wherein the illustrated device has a plurality of air channels and a non-central outlet.

DETAILED DESCRIPTION OF THE INVENTION

Figure 1C:
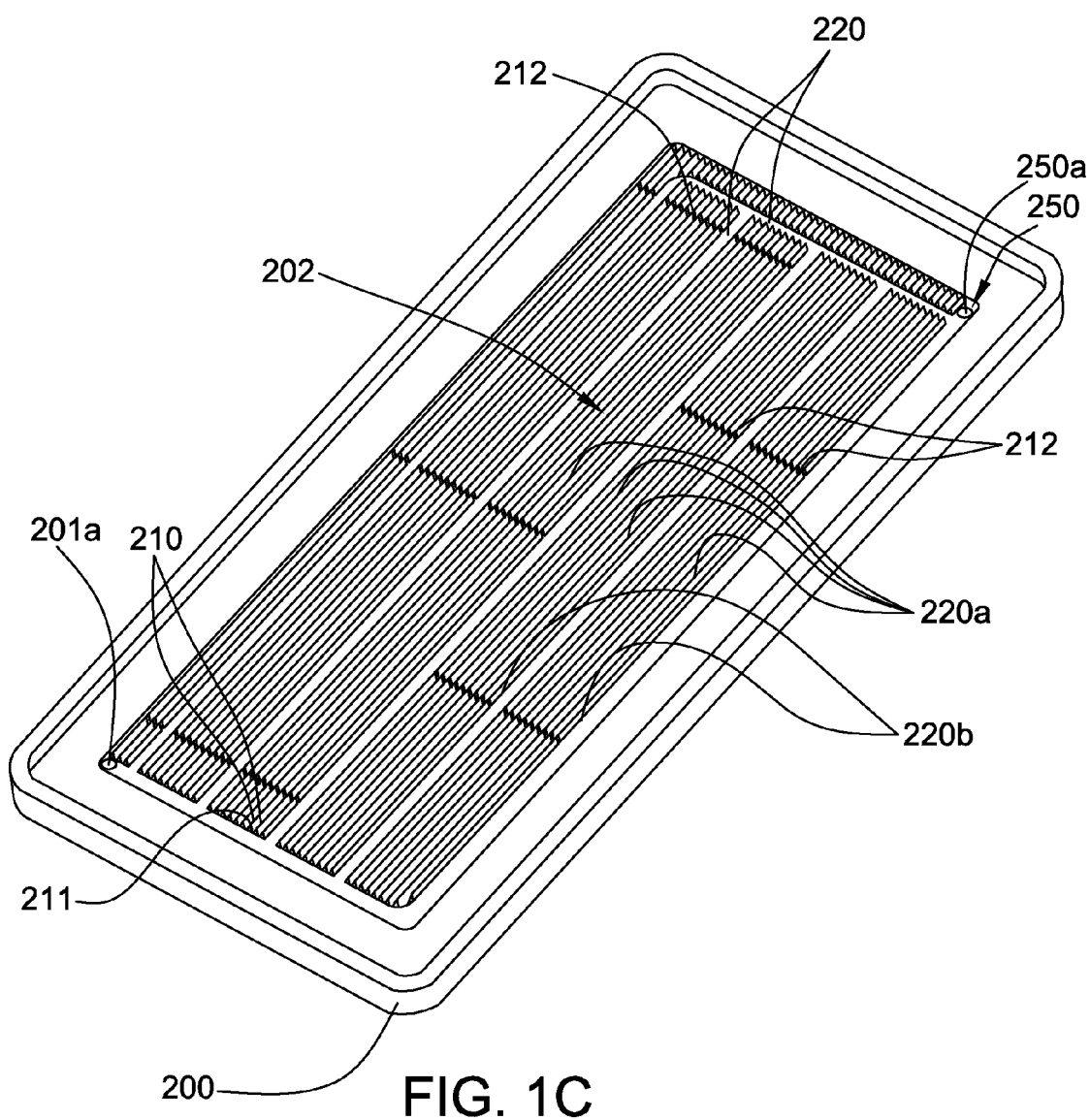
FIG. 1C shows a top view of the base.

Advantageously, the present invention provides for the isolation of a suitable volume of substantially cell-free liquid, e.g., cell-free plasma, preferably, from whole blood, e.g., unmodified and directly from a patient, without using a centrifuge, with minimal or no hemolysis of red blood cells, in a short period of time. The invention is particularly suitable for point of care (POC) applications. The invention can be carried out manually, automatically, or semi-automatically, e.g., wherein at least one aspect of the method (for example, applying the biological fluid to the surface of the filter) is carried out manually, and at least one other aspect (for example, creating a negative pressure) is automated.

In accordance with an embodiment of the present invention, a plasma separation device is provided comprising (a) a filter having an upstream surface and a downstream surface, the filter comprising a microporous membrane; and, (b) a housing, having an inlet, a downstream chamber, an outlet, and at least one air channel; defining a fluid flow path between the inlet, the downstream chamber, and the outlet, with the filter disposed in the housing across the fluid flow path, wherein the outlet and the air channel are spaced apart and are arranged such that, when a negative pressure is created in the downstream chamber through the outlet, air passes into the downstream chamber via the air channel and sweeps plasma from the downstream surface of the filter and through the outlet.

Preferably, the device includes one or more air channel inlet ports downstream of the downstream surface of the filter, wherein the air channel inlet port or ports communicate with one or more air channels.

In some embodiments of the device, the outlet is disposed near one end of the housing, and at least one air channel and at least one air channel inlet port are both disposed near the opposite end of the housing from the outlet (e.g., as shown in FIG. 1).

Embodiments of the device can include more than one filter, and the filter can include a plurality of porous layers and/or porous media. For example, the filter can comprise two or more membranes. Alternatively, or additionally, the filter can comprise at least one fibrous medium. Typically, in those embodiments including at least one fibrous medium, the fibrous medium is upstream of the membrane(s), e.g., the fibrous medium can act as a prefilter.

In a preferred embodiment, at least one membrane is an asymmetric microporous membrane having an upstream surface and a downstream surface and larger openings at the upstream surface than at the downstream surface.

A method for processing biological fluid according to an embodiment of the invention comprises applying biological fluid to the upstream surface of the filter of an embodiment of the plasma separation device; passing plasma from the upstream surface of the filter to the downstream surface of the filter via gravity; creating a negative pressure in the downstream chamber through the outlet; passing air through the air channel into the downstream chamber and sweeping plasma from the downstream surface of the filter; and, passing swept plasma through the outlet.

Embodiments of the invention are suitable for use with a variety of volumes of biological fluid. For example, the volume of biological fluid can be in the range of from about 100 µL to about 1 mL. However, the volume can be less than about 100 µL or greater than about 1 mL.

Each of the components of the invention will now be described in more detail below, wherein like components have like reference numbers.

In the illustrated embodiments (e.g., FIGS. 1D, 2C, and 3D), the plasma separation device 500 comprises a housing 400 comprising a first housing section or cover 100 comprising an inlet 101 (for applying biological fluid to the device), and a second housing section or base 200 comprising a downstream chamber 202 comprising plasma channels 220, and an outlet 201 including an outlet port 201a, and defining a fluid flow path between the inlet, the downstream chamber, and the outlet, the device also comprising a filter 600 comprising a porous membrane 650 (and optional fibrous medium 650a), the filter having an upstream surface 651 and a downstream surface 652, wherein the filter is disposed in the housing across the fluid flow path, and the downstream chamber 202 is downstream of the downstream surface 652 of the filter. Embodiments of the invention can include two or more filters and/or a filter can include two or more porous elements.

The device includes one or more air channels communicating with the downstream chamber, as well as (via one or more air channel inlet ports) the external environment of the device. The device can have two or more, three or more, or any other number of air channels and air channel ports. Preferably, the device housing includes one or more air channel inlet ports downstream of the downstream surface of the filter, wherein the outlet is spaced away from the air channel inlet port(s). In the embodiments of the invention illustrated in FIGS. 1-3 (e.g., FIGS. 1C, 2B, 2C, 3B, and 3C), the device housing includes one or more air channels 250 including air channel inlet ports 250a downstream of the downstream surface of the filter (wherein the base 200 comprises the illustrated air channels and air channel ports). Optionally, the device further comprises hydrophobic microporous membranes (not shown), e.g., covering the air channels, allowing air to enter the channels while preventing the entry of undesirable material such as particles and/or bacteria.

The illustrated embodiments of the device also include one or more plasma channels. For example, in the illustrated embodiments (e.g., FIGS. 1C and 2B), the downstream chamber 202 in the base comprises a plurality of plasma channels 220, the channels comprising ridges 220a and grooves 220b. The device can have any number of plasma channels. The plasma channels need not be uniform, e.g., with respect to shape, width, height and/or length between one channel and another and/or along any individual channel. For example, in the embodiment illustrated in FIG. 3C, the base 200 includes plasma channels of more than three different lengths (e.g., allowing "funneling" of plasma from the larger cross-sectional area near one end of the device to the smaller cross-sectional area near the other end of the device). In the embodiment illustrated in FIG. 1 (e.g., FIG. 1C), the plasma channels have a more uniform width and height (e.g., allowing more equalized air flow to sweep the downstream surface of the filter), and in the embodiment illustrated in FIG. 2 (e.g., FIG. 2B) the plasma channels have more uniform heights but different widths).

Preferably, the device includes a plurality of ridges supporting the downstream surface of the filter when a negative pressure is created, while allowing air to sweep plasma into the plasma channels. For example, in the illustrated embodiments shown in FIGS. 1C, 1D, and 2B, the base 200 includes ridges 210, providing auxiliary plasma channels 211, wherein the ridges support the downstream surface 652 of the filter (in the illustrated embodiment shown in FIG. 1D, porous membrane 650 has an upstream surface and a downstream surface, wherein the downstream surface of the membrane provides the downstream surface 652 of the filter, and optional fibrous medium 650a has an upstream surface and a downstream surface, wherein the upstream surface of the fibrous medium provides the upstream surface 651 of the filter). Optionally, as shown in FIG. 1C, the base also includes auxiliary plasma channels 212, e.g., to further improve efficiency of sweeping plasma into the plasma channels. In accordance with these illustrated embodiments, the auxiliary plasma channels 211 and 212 feed plasma into the main plasma channels 220.

The following definitions are used in accordance with the invention.

A filter comprising at least one porous filter element, e.g., at least one membrane and/or at least one fibrous element, can have any suitable pore structure, e.g., a pore size (for example, as evidenced by bubble point, or by $K_L$ as described in, for example, U.S. Pat. No. 4,340,479, or evidenced by capillary condensation flow porometry), a pore rating, a pore diameter (e.g., when characterized using the modified OSU F2 test as described in, for example, U.S. Pat. No. 4,925,572), or removal rating that reduces or allows the passage therethrough of one or more materials of interest as the plasma-containing fluid is passed through the element. The pore structure used depends on the composition of the fluid to be treated, and the desired effluent level of the treated fluid.

Suitable porous membranes, preferably microporous membranes, can be isotropic membranes, asymmetric membranes, membranes including both asymmetric and isometric regions and/or composite membranes. In those embodiments wherein the filter comprises an isotropic membrane, the filter typically further comprises a fibrous medium upstream of the isotropic membrane.

An isometric membrane has a porous structure with a distribution characterized by a pore structure (e.g., a mean pore size) that is substantially the same through the bulk of the membrane. For example, with respect to mean pore size, an isometric membrane has a pore size distribution characterized by a mean pore size that is substantially the same through the membrane.

An asymmetric membrane has a pore structure (e.g., a mean pore size) varying throughout the bulk of the membrane. For example, the mean pore size decreases in size from one portion or surface to another portion or surface (e.g., the mean pore size decreases from the upstream portion or surface to the downstream portion or surface). However, other types of asymmetry are encompassed by embodiments of the invention, e.g., the pore size goes through a minimum pore size at a position within the thickness of the asymmetric membrane. The asymmetric membrane can have any suitable pore size gradient or ratio. This asymmetry can be measured by, for example, comparing the mean pore size on one major surface of a membrane with the mean pore size of the other major surface of the membrane.

The pore structure of the filter elements is selected as is known in the art. Typically, the microporous membrane (or, for example, the downstream surface of an asymmetric microporous membrane) has a mean pore size in the range of about 5 micrometers to about 0.1 micrometers.

A variety of membranes and fibrous elements are suitable for use in the invention, including polymeric membranes and polymeric fibrous elements. Suitable polymers include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene difluoride (PVDF), polyethylene, polypropylene, polybutylene terephthalate (PBT), polyethylene terephthalate (PET), and any nylon, e.g., Nylon 6, 11, 46, 66, and 610. Preferred polymers are polysulfones, polyolefins, polyesters, and polyamides.

Other suitable materials include cellulosic derivatives, such as cellulose acetate, cellulose propionate, cellulose acetate-propionate, cellulose acetate-butyrate, and cellulose butyrate. Non-resinous materials, such as glass fibers, including, for example, borosilicate glass fibers, may also be used.

Particularly preferred are commercially available media, such as those membranes available from Pall Corporation under the trademarks VIVID™, SUPOR®, VERSAPOR®, and POSIDYNE®, as well as those available from Pall Corporation under the trademarks ULTIPOR $N_{66}$®, ULTIPOR®, FLUORODYNE®, LOPRODYNE®, CARBOXYDYNE®, IMMUNODYNE®, BIODYNE A®, BIODYNE B®, and BIODYNE C®.

Exemplary membranes are disclosed in, for example, U.S. Pat. Nos. 6,110,369; 6,045,899; 5,906,742; 5,979,670; and 5,846,422. Other membranes, including those disclosed in U.S. Pat. Nos. 4,702,840; 4,900,449; 4,906,374; 4,886,836; 4,964,989; 5,019,260; 4,340,479; 4,855,163; 4,744,132; 4,707,266; 4,203,848; 4,618,533; 6,039,872; 6,780,327; 6,783,937; and 7,189,322, may also be suitable.

Exemplary fibrous elements, including elements prepared from melt-blown fibers, are disclosed in, for example, U.S. Pat. Nos. 4,880,548, 4,925,572, 5,152,905, 5,443,743, 5,472,621, and 6,074,869. Suitable commercially available media include that available from Pall Corporation, for example, LEUKOSORB™, METRIGARD™, TISSUGLAST™ as well as glass and quartz fiber and microfiber media (binder-free or including binder) such as binder-free borosilicate glass grades A/B, A/C, A/D, A/E, and A/F.

The filter element, e.g., a membrane and/or a fibrous element, can have any desired critical wetting surface tension (CWST, as defined in, for example, U.S. Pat. No. 4,925,572). The CWST can be selected as is known in the art, e.g., as additionally disclosed in, for example, U.S. Pat. Nos. 5,152,905, 5,443,743, 5,472,621, and 6,074,869. Typically, the element has a CWST of greater than about 53 dynes/cm (about $53 \times 10^{-5}$ N/cm), more typically greater than about 58 dynes/cm (about $58 \times 10^{-5}$ N/cm), and can have a CWST of about 66 dynes/cm (about $66 \times 10^{-5}$ N/cm) or more. Preferably, the element is hydrophilic, having a CWST of 72 dynes/cm ($72 \times 10^{-5}$ N/cm) or more, in some embodiments, having a CWST of about 75 dynes/cm (about $75 \times 10^{-5}$ N/cm) or more.

The surface characteristics of the filter and/or filter element(s) can be modified (e.g., to affect the CWST, to include a surface charge, e.g., a positive or negative charge, and/or to alter the polarity or hydrophilicity of the surface) by wet or dry oxidation, by coating or depositing a polymer on the surface, or by a grafting reaction. Modifications include, e.g., irradiation, a polar or charged monomer, coating and/or curing the surface with a charged polymer, and carrying out chemical modification to attach functional groups on the surface. Grafting reactions may be activated by exposure to an energy source such as gas plasma, vapor plasma, corona discharge, heat, a Van der Graff generator, ultraviolet light, electron beam, or to various other forms of radiation, or by surface etching or deposition using a plasma treatment.

The filter, in some embodiments, comprising plurality of porous filter elements, is disposed in the housing comprising a biological fluid loading or application inlet and an outlet and a downstream chamber and defining at least one fluid flow path between the inlet and the downstream chamber and outlet, wherein the filter is across the fluid flow path, and the housing includes at least one air channel and at least one air channel inlet port, to provide a plasma separation device. Preferably, the separation device is sterilizable.

Figure 2A:
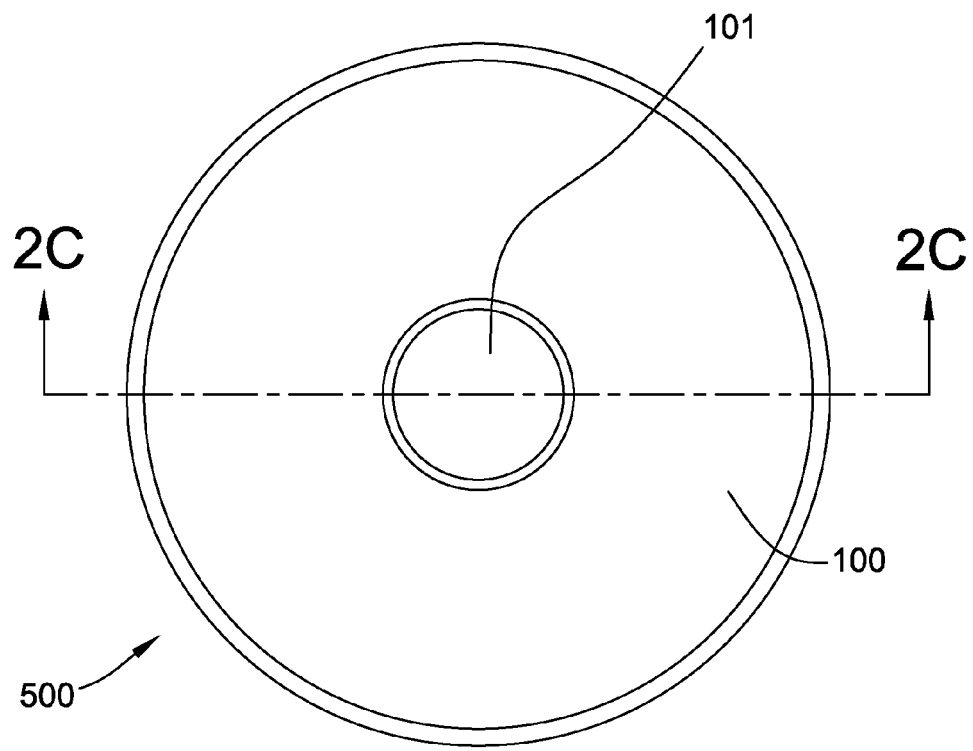
FIG. 2A shows a top view.
Figure 2C:
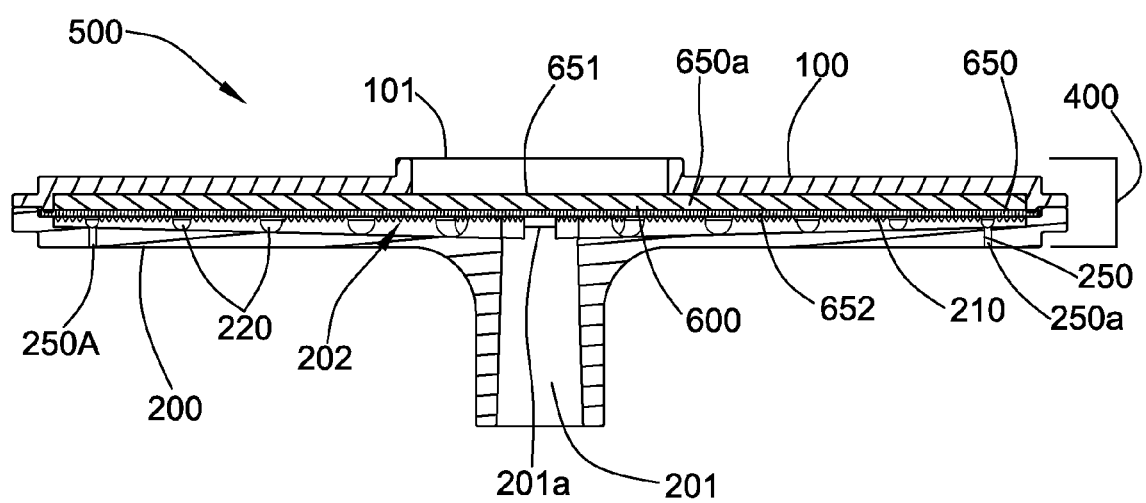
FIG. 2C shows a cross-sectional view, wherein the illustrated device has a plurality of air channels and a central outlet.
Figure 2B:
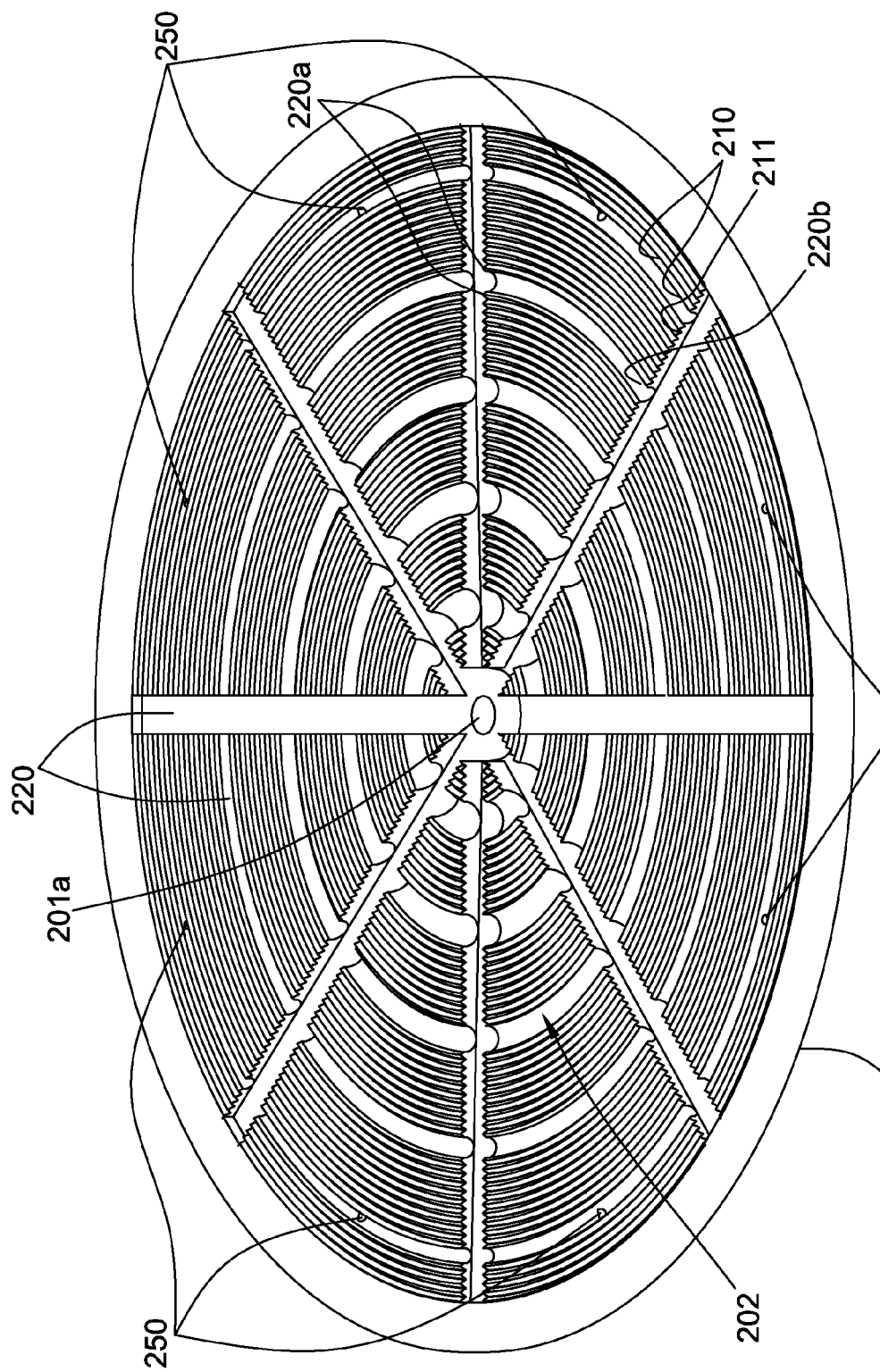
FIG. 2B shows a top view of the base.
Figure 3E:
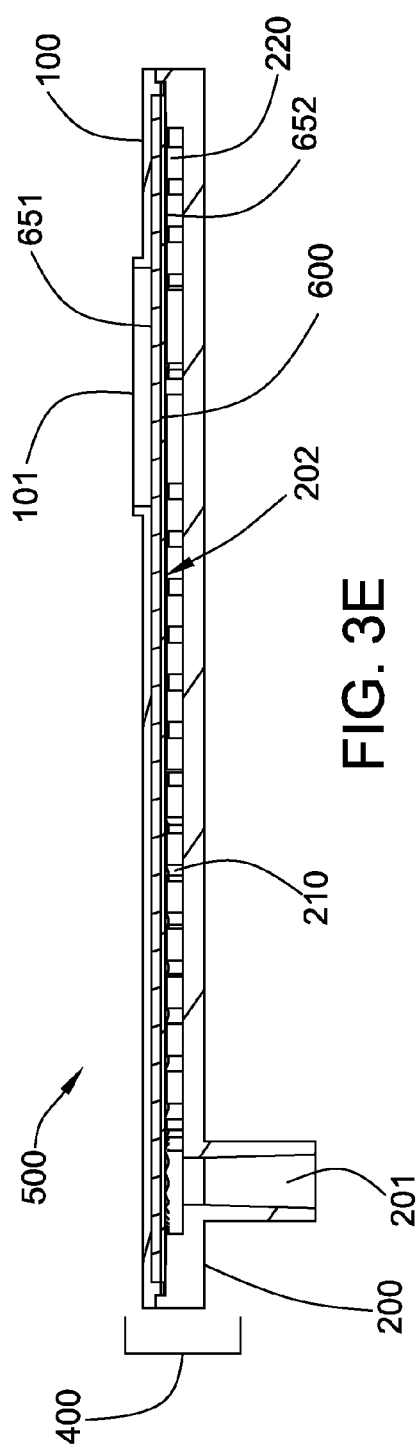
Figure 3B:
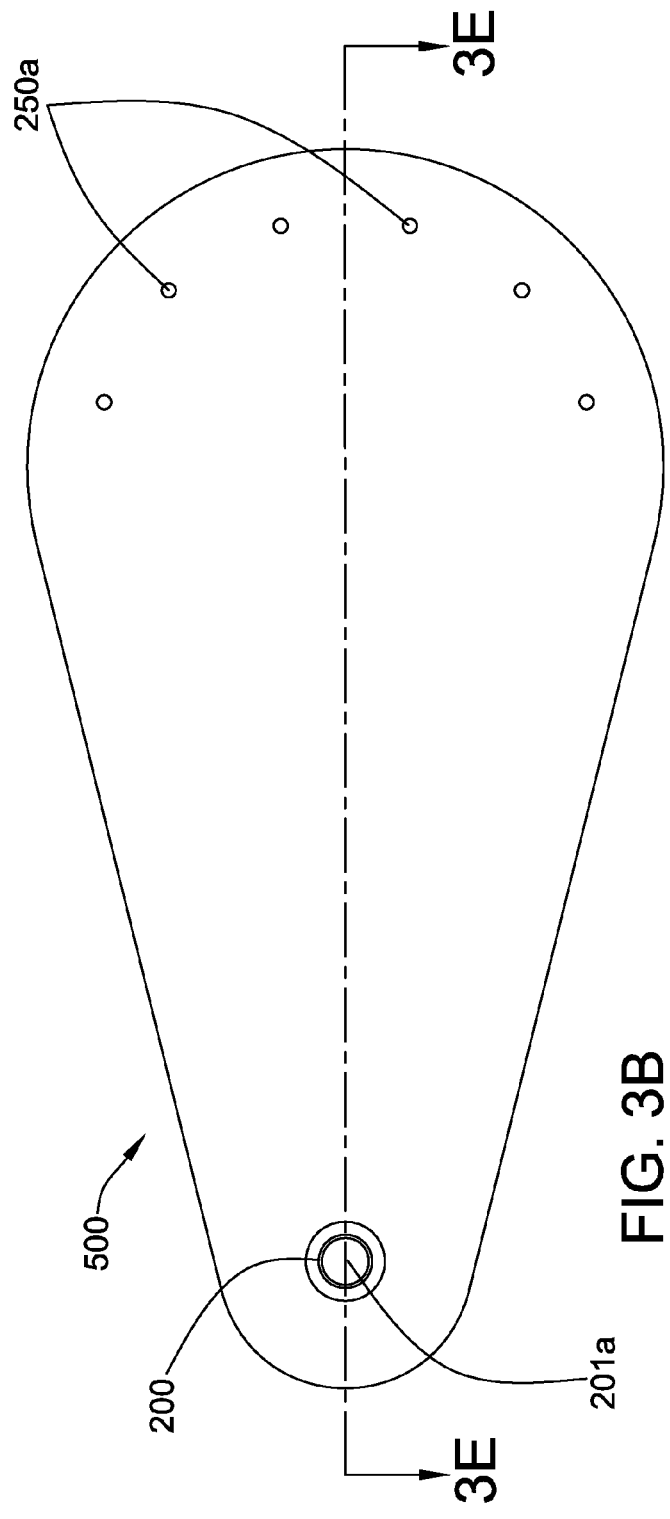

Any housing of suitable shape and providing an inlet, a downstream chamber, an outlet and at least one air channel and air channel inlet port, may be employed. Suitable shapes include, for example, generally teardrop (e.g., as shown in FIG. 3), rectangular (e.g., as shown in FIG. 1), square, circular (e.g., as shown in FIG. 2), oval, or triangular.

If desired, the housing can include one or more connectors. For example, the outlet can comprise a male or female connector (including a male or female luer fitting), a barbed connector, or a flange. A variety of connectors are suitable and are known in the art.

The housing can be fabricated from any suitable rigid impervious material, including any impervious thermoplastic material, which is compatible with the biological fluid being processed. Typically, the housing is fabricated from a polymer. In a preferred embodiment, the housing is a polymer, in some embodiments, a transparent or translucent polymer, such as an acrylic, polypropylene, polystyrene, or a polycarbonated resin. Such a housing is easily and economically fabricated, and allows observation of the passage of the biological fluid through the housing.

The housing can be sealed as is known in the art, utilizing, for example, one or more o-rings, an adhesive, a solvent, laser welding, radio frequency sealing, ultrasonic sealing and/or heat sealing. Additionally, or alternatively, the housing can be sealed via injection molding. The filter can be sealed within the housing as is known in the art, e.g., via o-rings, compression, interference fit, or bonded and/or welded to the housing.

Biological Fluid. A biological fluid includes any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); blood products derived from blood or a blood component or derived from bone marrow; stem cells; red cells separated from plasma and resuspended in a physiological solution or a cryoprotective fluid; and platelets separated from plasma and resuspended in a physiological solution or a cryoprotective fluid. The biological fluid may have been treated to remove some of the leukocytes before being processed according to the invention. As used herein, blood product or biological fluid refers to the components described above, and to similar blood products or biological fluids obtained by other means and with similar properties.

A variety of devices and/or systems are suitable for creating a negative pressure in the downstream chamber through the outlet and are known to one of ordinary skill in the art. For example, a syringe, e.g., comprising a barrel and plunger, can be used. Alternatively, for example, one or more of a manifold plate, adapter, and/or a vacuum system (including, for example, a vacuum tube blood collection system) can be used.

In accordance with a typical embodiment of a method according to the invention, a biological fluid is applied to the upstream surface of the filter of an embodiment of the device, and liquid (e.g., plasma) passes from the upstream surface of the filter to the downstream surface of the filter. Typically, the liquid passes from the upstream surface of the filter to the downstream surface of the filter primarily via gravity, but the effect of gravity can also be assisted by the creation of a negative pressure created in the downstream chamber. Shortly after applying the biological fluid to the filter (e.g., after at least about 30 seconds), a negative pressure is created in the downstream chamber through the outlet (e.g., by withdrawing a plunger within a syringe barrel communicating with an outlet of the device housing); and air passes through the air channel into the downstream chamber, sweeping substantially cell-free liquid (e.g., substantially cell-free plasma) from the downstream surface of the filter; and, swept liquid passes through the outlet. In one illustrative embodiment, the swept plasma is passed into the syringe barrel communicating with the outlet, and in another illustrative embodiment, the swept plasma is passed into the vacuum blood collection tube communicating with the outlet.

The swept collected liquid can be further processed as desired and as known to one of skill in the art. For example, one or more assays can be carried out using the plasma, e.g., wherein the plasma is mixed with one or more reagents and/or placed in or on an analytical device.

The following examples further illustrate the invention but, of course, should not be construed as in any way limiting its scope.

Examples 1-14 are carried out using the embodiment of the device as generally illustrated in FIG. 1 (with or without an upstream fibrous medium as noted below). The media used to provide the filter are 35 mm×65 mm. In those examples including an asymmetric membrane, the membrane is a Vivid™ (Pall Corporation, East Hills, N.Y.) asymmetric polysulfone plasma separation membrane (PSM) having a mean pore size of about 100 μm on one side, and about 2 μm on the other side (asymmetry ratio of about 100:2), used with the larger pore size facing upstream side of the device.

The biological fluid used is blood drawn from a healthy donor into 7 mL Vacutainer® (Becton-Dickinson) blood collection tubes containing EDTA anticoagulant. The blood, which has a hematocrit of about 35%, is used within about 2 hours of collection.

The blood is loaded onto the surface of the filter using a pipette, and after about 60 to about 90 seconds, a syringe is operated to provide a negative pressure. Plasma is separated and collected within about 2 minutes of loading. The volume of recovered plasma is measured.

In Examples 1-10, the collected plasma is analyzed to determine the plasma cholesterol (% recovery as compared to the control), total protein (% recovery as compared to the control), and free hemoglobin (% recovery as compared to the control), and the values are compared to plasma separated and collected using centrifugation (the control). SD=standard deviation.

In Examples 1-14, the collected plasma is analyzed for residual cellular components using a Cell-DYN® 3700 analyzer (Abbott Diagnostics, Abbott Park, Ill.), and the concentrations of the red blood cells, white blood cells, and platelets are lower than the detection limit of the instrument.

These examples demonstrate that cell-free plasma can be quickly separated from blood in accordance with embodiments of the invention.

EXAMPLE 1

This example demonstrates that cell-free plasma can be quickly separated from blood without significantly adversely affecting the plasma cholesterol, total protein, and free hemoglobin using an embodiment of a device including a single membrane.

The membrane is a Vivid™ PSM grade GF asymmetric polysulfone membrane. The results are as follows.

| vol blood μL | vol plasma μL | cholesterol | SD cholesterol | total protein | SD total protein | free hemoglobin |
|---|---|---|---|---|---|---|
| 850 | 55 | 101 | 1 | 102 | 2 | 102 |

EXAMPLE 2

This example demonstrates that cell-free plasma can be quickly separated from blood without significantly adversely affecting the plasma cholesterol, total protein, and free hemoglobin using an embodiment of a device including a membrane and a fibrous element upstream of the membrane.

The membrane is a Vivid™ PSM grade GF asymmetric polysulfone membrane. The fibrous element is a layer of binder-free borosilicate glass fibers grade A/D (Pall Corporation, East Hills, N.Y.) having a mean pore size of 3.1 μm and a thickness of between about 584 to about 737 μm (about 23 to about 29 mils). The results are as follows.

| vol blood μL | vol plasma μL | cholesterol | SD cholesterol | total protein | SD total protein | free hemoglobin |
|---|---|---|---|---|---|---|
| 2800 | 700 | 101 | 3 | 101 | 1 | 103 |

EXAMPLE 3

This example demonstrates that cell-free plasma can be quickly separated from blood without significantly adversely affecting the plasma cholesterol, total protein, and free hemoglobin using an embodiment of a device including a membrane and a fibrous element upstream of the membrane.

The membrane is a Vivid™ PSM grade GF asymmetric polysulfone membrane. The fibrous element is a layer of Leukosorb™ media (Pall Corporation, East Hills, N.Y.) having a mean pore size of about 8 μm and a thickness of between about 356 to about 559 μm. The results are as follows.

| vol blood μL | vol plasma μL | cholesterol | SD cholesterol | total protein | SD total protein | free hemoglobin |
|---|---|---|---|---|---|---|
| 1600 | 280 | 103 | 2 | 100 | 1 | 106 |

EXAMPLE 4

This example demonstrates that cell-free plasma can be quickly separated from blood without significantly adversely affecting the plasma cholesterol, total protein, and free hemoglobin using an embodiment of a device including a single membrane.

The membrane is a Vivid™ PSM grade GX asymmetric polysulfone membrane. The results are as follows.

| vol blood μL | vol plasma μL | cholesterol | SD cholesterol | total protein | SD total protein | free hemoglobin |
|---|---|---|---|---|---|---|
| 850 | 724 | 101 | 3 | 101 | 1 | 108 |

EXAMPLE 5

This example demonstrates that cell-free plasma can be quickly separated from blood without significantly adversely affecting the plasma cholesterol, total protein, and free hemoglobin using an embodiment of a device including a membrane and a fibrous element upstream of the membrane.

The membrane is a Vivid™ PSM grade GX asymmetric polysulfone membrane. The fibrous element is a layer of binder-free borosilicate glass fibers grade A/D (Pall Corporation, East Hills, N.Y.) having a mean pore size of 3.1 μm and a thickness of between about 584 to about 737 μm (about 23 to about 29 mils). The results are as follows.

| vol blood μL | vol plasma μL | cholesterol | SD cholesterol | total protein | SD total protein | free hemoglobin |
|---|---|---|---|---|---|---|
| 2800 | 704 | 98 | 1 | 101 | 5 | 101 |

EXAMPLE 6

This example demonstrates that cell-free plasma can be quickly separated from blood without significantly adversely affecting the plasma cholesterol, total protein, and free hemoglobin using an embodiment of a device including a membrane and a fibrous element upstream of the membrane.

The membrane is a Vivid™ PSM grade GX asymmetric polysulfone membrane. The fibrous element is a layer of Leukosorb™ media (Pall Corporation, East Hills, N.Y.) having a mean pore size of about 8 μm and a thickness of between about 356 to about 559 μm. The results are as follows.

| vol blood μL | vol plasma μL | cholesterol | SD cholesterol | total protein | SD total protein | free hemoglobin |
|---|---|---|---|---|---|---|
| 1600 | 325 | 95 | 1 | 92 | 4 | 98 |

EXAMPLE 7

This example demonstrates that cell-free plasma can be quickly separated from blood without significantly adversely affecting the plasma cholesterol, total protein, and free hemoglobin using an embodiment of a device including a single membrane.

The membrane is a Vivid™ PSM grade GR asymmetric polysulfone membrane. The results are as follows.

| vol blood μL | vol plasma μL | cholesterol | SD cholesterol | total protein | SD total protein | free hemoglobin |
|---|---|---|---|---|---|---|
| 850 | 292 | 95 | 1 | 90 | 2 | 100 |

EXAMPLE 8

This example demonstrates that cell-free plasma can be quickly separated from blood without significantly adversely affecting the plasma cholesterol, total protein, and free hemoglobin using an embodiment of a device including a membrane and a fibrous element upstream of the membrane.

The membrane is a Vivid™ PSM grade GR asymmetric polysulfone membrane. The fibrous element is a layer of binder-free borosilicate glass fibers grade A/D (Pall Corporation, East Hills, N.Y.) having a mean pore size of 3.1 μm and a thickness of between about 584 to 737 μm (about 23 to about 29 mils). The results are as follows.

| vol blood μL | vol plasma μL | cholesterol | SD cholesterol | total protein | SD total protein | free hemoglobin |
|---|---|---|---|---|---|---|
| 2800 | 730 | 78 | 3 | 90 | 2 | 98 |

EXAMPLE 9

This example demonstrates that cell-free plasma can be quickly separated from blood without significantly adversely affecting the plasma cholesterol, total protein, and free hemoglobin using an embodiment of a device including a membrane and a fibrous element upstream of the membrane.

The membrane is a Vivid™ PSM grade GR asymmetric polysulfone membrane. The fibrous element is a layer of Leukosorb™ media (Pall Corporation, East Hills, N.Y.) having a mean pore size of about 8 μm and a thickness of between about 356 to about 559 μm. The results are as follows.

| vol blood μL | vol plasma μL | cholesterol | SD cholesterol | total protein | SD total protein | free hemoglobin |
|---|---|---|---|---|---|---|
| 1600 | 322 | 90 | 1 | 95 | 2 | 102 |

EXAMPLE 10

This example demonstrates that cell-free plasma can be quickly separated from blood without significantly adversely affecting the plasma cholesterol, total protein, and free hemoglobin using an embodiment of a device including a membrane and a fibrous element upstream of the membrane.

The membrane is an isotropic Supor® 450 polyethersulfone membrane (Pall Corporation, East Hills, N.Y.) having a mean pore size of about 0.45 μm and a thickness of between about 114 to about 165 μm. The fibrous element is a layer of binder-free borosilicate glass fibers grade A/D (Pall Corporation, East Hills, N.Y.) having a mean pore size of 3.1 μm and a thickness of between about 584 to 737 μm (about 23 to about 29 mils). The results are as follows.

| vol blood μL | vol plasma μL | cholesterol | SD cholesterol | total protein | SD total protein | free hemoglobin |
|---|---|---|---|---|---|---|
| 2800 | 260 | 101 | 3 | 101 | 1 | 110 |

EXAMPLE 11

This example demonstrates that cell-free plasma can be quickly separated from blood using embodiments of devices including a membrane and a fibrous element upstream of the membrane.

Both devices include a fibrous element upstream of the membrane which is a layer of binder-free borosilicate glass fibers grade A/D (Pall Corporation, East Hills, N.Y.) having a mean pore size of 3.1 μm and a thickness of between about 584 to 737 μm (about 23 to about 29 mils).

For one device, the membrane is an isotropic Supor® 200 polyethersulfone membrane (Pall Corporation, East Hills, N.Y.) having a mean pore size of about 0.20 μm and a thickness of between about 114 to about 165 μm. For the other device, the membrane is an isotropic Supor® 1200 membrane (Pall Corporation, East Hills, N.Y.) having a mean pore size of about 1.2 μm and a thickness of between about 114 to about 165 μm.

The results are as follows.

Device Including Supor® 200 Polyethersulfone Membrane

| vol blood μL | vol plasma μL |
|---|---|
| 2700 | 250 |

Device Including Supor® 1200 Polyethersulfone Membrane

| vol blood μL | vol plasma μL |
|---|---|
| 2700 | 355 |

EXAMPLE 12

This example demonstrates that cell-free plasma can be quickly separated from blood embodiment of devices including a membrane and a fibrous element upstream of the membrane.

Both devices include a fibrous element upstream of the membrane which is a layer of binder-free borosilicate glass fibers grade A/D (Pall Corporation, East Hills, N.Y.) having a mean pore size of 3.1 μm and a thickness of between about 584 to 737 μm (about 23 to about 29 mils).

For one device, the membrane is an isotropic Supor® 450 polyethersulfone membrane (Pall Corporation, East Hills, N.Y.) having a mean pore size of about 0.45 μm and a thickness of between about 114 to about 165 μm. For the other device, the membrane is an isotropic Fluorodyne® II PVDF membrane (Pall Corporation, East Hills, N.Y.) having a mean pore size of about 0.45 μm.

The results are as follows.

Device Including Supor® 450 Polyethersulfone Membrane

| vol blood μL | vol plasma μL |
|---|---|
| 2700 | 280 |

Device Including Fluorodyne® II PVDF Membrane

| vol blood μL | vol plasma μL |
|---|---|
| 2700 | 336 |

EXAMPLE 13

This example demonstrates that cell-free plasma can be quickly separated from blood embodiment of devices including a membrane and different fibrous media upstream of the membrane. The membrane in each device is a Vivid™ PSM grade GR asymmetric polysulfone membrane.

One device included a layer of binder-free borosilicate glass fibers grade A/D (Pall Corporation, East Hills, N.Y.) having a mean pore size of 3.1 μm and a thickness of between about 584 to 737 μm (about 23 to about 29 mils).

The other device included a layer of binder-free borosilicate glass fibers grade A/B (Pall Corporation, East Hills, N.Y.) having a mean pore size of 1 μm and a thickness of between about 610 to 711 μm (about 24 to about 28 mils).

The results are as follows.

Device Including Borosilicate Glass Fibers Grade A/D

| vol blood μL | vol plasma μL |
|---|---|
| 2700 | 720 |

Device Including Borosilicate Glass Fibers Grade A/B

| vol blood μL | vol plasma μL |
|---|---|
| 2700 | 780 |

EXAMPLE 14

This example demonstrates that cell-free plasma can be quickly separated from blood embodiment of devices including a membrane and fibrous elements including different thicknesses upstream of the membrane.

The membrane is a Vivid™ PSM grade GR asymmetric polysulfone membrane. The fibrous elements are one or four layers of Leukosorb™ media (Pall Corporation, East Hills, N.Y.) having a mean pore size of about 8 μm and a thickness of between about 356 to about 559 μm for each layer. The results are as follows.

Device Including One Layer of Leukosorb™ Media

| vol blood μL | vol plasma μL |
|---|---|
| 1600 | 505 |

Device Including Four Layers of Leukosorb™ Media

| vol blood μL | vol plasma μL |
|---|---|
| 2700 | 306 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A plasma separation device comprising:
   (a) a filter having an upstream surface and a downstream surface, the filter comprising a microporous membrane; and,
   (b) a housing, having an inlet, a downstream chamber, and an outlet, the housing comprising a base comprising the downstream chamber and the outlet and two or more air channels, wherein the base further comprises at least one plasma channel in fluid communication with the outlet; defining a fluid flow path between the inlet, the downstream chamber, and the outlet, with the filter disposed in the housing across the fluid flow path, wherein the outlet and the air channels are spaced apart and are arranged such that, when a negative pressure is created in the downstream chamber through the outlet, air passes into the downstream chamber via the air channels and sweeps plasma from the downstream surface of the filter and through the outlet.

2. The device of claim 1, wherein the outlet and at least one air channel are respectively disposed near opposite ends of the base.

3. The device of claim 1, wherein the membrane is an asymmetrical membrane having larger openings at the upstream surface than at the downstream surface.

4. The device of claim 1, wherein filter includes a plurality of porous media.

5. The device of claim 4, wherein the filter includes the membrane and a fibrous medium.

6. The device of claim 5, wherein the fibrous medium includes glass fibers.

7. The device of claim 5, wherein the fibrous medium includes melt-blown fibers.

8. A method of separating plasma from biological fluid, the method comprising:

obtaining a plasma separation device comprising a filter having an upstream surface and a downstream surface, the filter comprising a microporous membrane; and, a housing, having an inlet, a downstream chamber, and an outlet, and at least one air channel; defining a fluid flow path between the inlet, the downstream chamber, and the outlet, with the filter disposed in the housing across the fluid flow path, wherein the outlet and the air channel are spaced apart and are arranged such that, when a negative pressure is created in the downstream chamber through the outlet, air passes into the downstream chamber via the air channel and sweeps plasma from the downstream surface of the filter and through the outlet; and, applying biological fluid to the upstream surface of the filter;

passing plasma from the upstream surface of the filter to the downstream surface of the filter;

creating a negative pressure in the downstream chamber through the outlet;

passing air through the air channel into the downstream chamber and sweeping plasma from the downstream surface of the filter; and, passing swept plasma through the outlet.

9. The method of claim 8, wherein the plasma separation device comprises a housing comprising a base comprising the downstream chamber and the outlet and two or more air channels, the base further comprising at least one plasma channel in fluid communication with the outlet, wherein the outlet and the air channels are spaced apart; the negative pressure including passing air through the air channels into the downstream chamber and sweeping plasma from the downstream surface of the filter; and, passing swept plasma through the outlet.

* * * * *